United States Patent [19]

Néel et al.

[11] Patent Number: 4,622,104
[45] Date of Patent: Nov. 11, 1986

[54] PROCESS FOR THE RECOVERY OF ETHYLENE GLYCOL IN CONCENTRATED FORM

[75] Inventors: Henri Néel, Le Havre; Francis Delannoy, Pierre-Benite, both of France

[73] Assignee: Atochem, France

[21] Appl. No.: 631,166

[22] Filed: Jul. 16, 1984

[30] Foreign Application Priority Data

May 15, 1984 [FR] France ............... 84 07695

[51] Int. Cl.$^4$ ............................................. B01D 3/00
[52] U.S. Cl. ....................................... 203/18; 203/37; 203/73; 203/78; 203/80; 568/868
[58] Field of Search ............ 203/7, 34, 11, 36, 14, 203/18, 71, 73, 75, 77, 78, 80, 84, 37; 568/867, 868, 869, 871; 549/538; 55/51

[56] References Cited

U.S. PATENT DOCUMENTS

| | | | |
|---|---|---|---|
| 2,839,588 | 6/1958 | Parker | 568/867 |
| 3,904,656 | 9/1975 | Brez | 568/867 |
| 3,922,314 | 11/1975 | Cocuzza et al. | 203/63 |
| 3,970,711 | 7/1976 | Reiche et al. | 568/868 |
| 4,033,617 | 7/1977 | Cocuzza et al. | 549/538 |
| 4,182,659 | 1/1980 | Anwer et al. | 203/18 |
| 4,349,417 | 9/1982 | Rebsdat et al. | 203/71 |

FOREIGN PATENT DOCUMENTS

| | | | |
|---|---|---|---|
| 45-10324 | 4/1970 | Japan | 568/867 |
| 6118024 | 9/1981 | Japan | 568/867 |
| 1463324 | 2/1977 | United Kingdom . | |

*Primary Examiner*—S. Leon Bashore
*Assistant Examiner*—V. Manoharan
*Attorney, Agent, or Firm*—Sigalos & Levine

[57] ABSTRACT

A process for the separation of ethylene glycol from glycolated water obtained from the bottom of an ethylene oxide desorption column in a process for the manufacture of ethylene oxide by catalytic oxidation of ethylene by oxygen in the vapor phase, comprising feeding said glycolated water directly from the bottom of said ethylene oxide desorption column into the top of a separation column having therebelow up to 12 theoretical plates and adding sufficient indirect heat to said glycolated water to form two streams; a first gaseous stream consisting essentially of steam which is removed from the top of said separation column and introduced into said ethylene oxide desorption column to serve therein as the desorption fluid, and a second aqueous stream containing from about 40% to 90% by weight of ethylene glycol which is removed from the bottom of said separation column.

3 Claims, No Drawings

PROCESS FOR THE RECOVERY OF ETHYLENE GLYCOL IN CONCENTRATED FORM

BACKGROUND OF THE INVENTION

The present invention concerns a process for recovering ethylene glycol formed in a method for the manufacture of ethylene oxide by the catalytic oxidation in the gaseous phase of ethylene with oxygen.

The two first steps customarily adopted in order to isolate the ethylene oxide from the gaseous mixture resulting from such a reaction are:

(1) An absorption consisting of placing the gaseous mixture in contact with water in order to form a dilute aqueous ethylene oxide solution containing gases in the dissolved state and especially carbon dioxide; and (2) A desorption consisting of subjecting the aqueous ethylene oxide solution resulting from the absorption step to the action of steam in a column delivering at the bottom an aqueous stream practically devoid of ethylene oxide serving, after cooling, as absorption fluid in the first of the two steps just described.

This aqueous stream, designated in the description which follows by the expression "37 glycolated water", becomes progressively and continuously enriched in ethylene glycol formed by hydration of the ethylene oxide under the conditions to which this compound is subjected; particularly during the desorption stage, if a part were not evacuated from it in order to limit the concentration of ethylene glycol to a value generally not exceeding about 10% by weight.

The economics of the process for the manufacture of ethylene oxide, including pollution problems, demand that the ethylene glycol contained in the evacuated glycolated water be recovered.

In practice, amongst other things, glycolated water contains, besides ethylene glycol, other glycols such as diethylene glycol or triethylene glycol, troublesome impurities such as those pointed out in U.S. Pat. No. 3,904,656 and salts, principally sodium or potassium carbonates and sodium or potassium salts of carboxylic acids. The presence of these salts is due to the addition of anticorrosive sodium or potassium compounds, such as hydroxides, to the glycolated water which otherwise would produce corrosion phenomena, its ph being normally rendered acidic by the carbon dioxide and the carboxylic acids which it contains.

In order to separate the ethylene glycol from the stream of glycolated water evacuated from the cycle, the known processes recommend complex and expensive treatments.

Thus, U.S. Pat. No. 3,904,656 recommends the passage of the evacuated glycolated solution over ion exchange resins and over activated charcoal prior to directing the aqueous stream resulting from this treatment and containing the ethylene glycol toward a step of a process for the manufacture of ethylene glycol from ethylene oxide.

For its part, French Pat. No. 2,246,527 describes a treatment of evacuated glycolated water by inverse osmosis delivering on one hand an aqueous stream containing about 60% of the ethylene glycol initially contained in it and practically no longer any salts, and on the other hand an aqueous stream containing practically the entire salts and the complement of the ethylene glycol. The first one of the two aqueous streams is introduced into an installation for the production of glycol. The ethylene glycol contained in the second aqueous stream is not recovered.

According to French Pat. No. 2,295,938, the ethylene glycol is separated from the evacuated glycolated solution by placing the latter in contact with cation exchangers and anion exchangers prior to the separation of the glycols by distillation.

None of the known procedures realizes the separation of ethylene glycol in the concentrated form, directly from the evacuated glycolated water and without prior separation of the salts which it contains.

SUMMARY OF THE INVENTION

The present invention solves these problems by providing a process for separating concentrated ethylene glycol from the evacuated glycolated water stream without prior separation of the salts contained therein.

Briefly, the present invention comprises a process for the separation of ethylene glycol from glycolated water obtained from the bottom of an ethylene oxide desorption column in a process for the manufacture of ethylene oxide by catalytic oxidation of ethylene by oxygen in the vapor phase, comprising feeding said glycolated water directly from the bottom of said ethylene oxide desorption column into the top of a separation column having therebelow up to 12 theoretical plates and adding sufficient indirect heat to said glycolated water to form two streams; a first gaseous stream consisting essentially of steam which is removed from the top of said separation column and introduced into said ethylene oxide desorption column to serve therein as the extraction stream, and a second aqueous stream containing from about 40% to 90% by weight of ethylene glycol which is removed from the bottom of said separation column.

DETAILED DESCRIPTION

Preferably, the glycolated water fraction to be treated in accordance with the present invention is introduced into the ethylene glycol separation column under the temperature and pressure conditions which are those or which are similar to those in which the glycolated water is found when leaving the desorption column.

The presence of salts commonly present in glycolated water does not hinder at all the carrying out of the process of the invention.

The mean absolute pressure in the column of the process of the invention is at least equal to the one of the ethylene oxide desorption column. It is most often below 6 bars.

The temperature in the column depends on this pressure and on the desired concentration in the stream issuing from the bottom of the column which contains the ethylene glycol and salts separated from the treated glycolated water fraction.

The heat is furnished to the column with the help of, for instance, steam or any conventional heating fluid.

The stream issuing from the bottom of the column and which contains the ethylene glycol, subsequently to being obtained can be treated in any conventional and known manner in order to isolate the concentrated ethylene glycol, for instance, by eliminating the water, then distilling of the ethylene glycol in a film type evaporator. For the same purpose, prior to isolations it can be united with a stream containing ethylene glycol in a process for the manufacture of this compound from ethylene oxide.

The invention will be further described in connection with the following examples which are set forth for the purposes of illustration only.

EXAMPLE 1

From a conventional system for the manufacture of ethylene oxide by catalytic oxidation in the vapor phase of the ethylene by oxygen, which includes an ethylene oxide isolation system comprising a column for the absorption by water of the ethylene oxide contained in the gaseous mixture issuing from the zone of catalysis and a column for the desorption by the water vapor of the ethylene oxide thus absorbed, there is taken 387.1 kg/h of an aqueous stream containing by weight 94.4% of water, 2.54% of ethylene oxide and 3% of ethylene glycol. This stream is introduced at a temperature of 108° C. into the desorption column comprising 5 theoretical plates. At the top of this column there leave 23.9 kg/h of a gaseous mixture at a temperature of 97° C. and at an absolute pressure of 1.2 bars, which contain by weight 58% of water and 40.5% of ethylene oxide besides principally gases such as carbon dioxide initially present in the dissolved state in the dilute agueous solution of ethylene oxide introduced into the desorption column.

The stream of glycolated water issuing at 109° C. at the bottom of the desorption column at a rate of 376.2 kg/h contains by weight 3.1% of ethylene glycol and less than 0.01% of ethylene oxide. It is then divided into two parts; the first one of which, or 362.5 kg/h, after cooling serves as absorption current for the ethylene oxide in the first of the two columns cited at the beginning of this example.

The second part, or 13.74 kg/h, is introduced at a temperature of 109° C. at the upper level of a glycolated water treatment column comprising 2 theoretical plates.

The gaseous stream from the top of this column, at a temperature of 109.5° C., at an absolute pressure of 1.4 bars and at a flow rate of 13.07 kg/h, practically consists of steam and is introduced into the desorption column from where the glycolated water is obtained in order to serve there as desorption fluid for the ethylene oxide.

The aqueous stream issued from the bottom of the glycolated water treatment column at a flow rate of 0.67 kg/h and at a temperature of 120.5° C. contains 60% by weight of ethylene glycol.

Such a result of ethylene glycol concentration and of effectiveness of ethylene oxide recovery requires that 1.5 thermies/hour be furnished to the ethylene glycol desorption column and 7 thermies/hour be furnished to the glycolated water treatment column.

At an identical ethylene oxide desorption effectiveness, an equivalent amount of heat energy leads only to obtaining of the ethylene glycol in the form of a dilute aqueous solution containing only 3.1% of ethylene glycol by weight when the process of the invention is not being utilized.

EXAMPLE 2

By operating the desorption of the ethylene oxide as in Example 1, but by drawing off at the top of the column at a temperature of 137.5° C. and at an absolute pressure of 5 bars, 18.9 kg/h of a gaseous stream containing by weight 51% of ethylene oxide and 47% of water, 383.9 kg/h of glycolated water containing 3.3% by weight of ethylene glycol and less than 0.01% by weight of ethylene oxide are drawn off at the bottom of the column at a temperature of 153° C. 16.41 kg/h of glycolated water are introduced at that temperature into the same column as in Example 1 in order to be subjected to the treatment according to the invention. 15.74 kg/h of a gaseous stream essentially consisting of steam are issued from the top of the column, at a temperature of 154° C. and at an absolute pressure of 5.2 bars, and then are introduced into the ethylene glycol desorption column.

At the bottom of the column, the ethylene glycol is collected at 166° C. in the form of an aqueous stream flowing at 0.67 kg/h and containing 60% of ethylene glycol by weight.

This result is obtained without it having been necessary to furnish to the system an amount of heat energy greater than that which the system would have necessitated not including the treatment of the invention and ensuring the same effectiveness of desorption of the ethylene oxide, but only the obtaining of a dilute aqueous solution of ethylene glycol containing only 3.3% by weight of this product.

EXAMPLE 3

The aqueous stream of Example 1, from which the ethylene oxide must be desorbed, is introduced at the same flow rate, at the same temperature and into the same column as in Example 1.

23.2 kg/h of a gaseous stream containing by weight 42% of ethylene oxide and 56.5% of water are issued from the top of the column at an absolute pressure of 3 bars and at a temperature of 124° C.

At the bottom of the column there leave 395.4 kg/h of glycolated water containing by weight 3.2% of ethylene glycol at a temperature of 135° C.

31.9 kg/h of glycolated water are introduced at that temperature into the same treatment column according to the invention as in Example 1.

At the top of this column there issue 31.46 kg/h of a gaseous current essentially consisting of steam, at a temperature of 136° C., which refers back to 31.46 kg/h and which are introduced at this temperature into the ethylene oxide desorption column.

The ethylene glycol is recovered with water, at the bottom of the glycolated water treatment column at a temperature of 180° C., in the form of a stream containing 90% by weight of ethylene glycol, at a flow rate of 0.445 kg/h.

The amount of heat input (thermal energy) furnished is equivalent to the one ensuring the same effectiveness of desorption of ethylene oxide in a system not including the treatment of glycolated water according to the invention and delivering the ethylene glycol in the form of an aqueous solution containing only 3.2% of ethylene glycol by weight.

EXAMPLE 4

By operating as in Example 1, but by introducing into the ethylene oxide desorption column at a temperature of 108° C., 403.7 kg/h of an aqueous stream containing by weight, besides 90.5% of water, 2,44% of ethylene oxide and 7% of ethylene glycol; 17.9 kg/h of a gaseous stream, at a temperature of 120° C. and at an absolute pressure of 3 bars are issued from the top of the column. They contain by weight 54% of ethylene oxide and 44% of water.

At the bottom of the column 393.4 kg/h of glycolated water are withdrawn, at a temperature of 135.5° C., which contain 7.3% by weight of ethylene glycol.

8.1 kg/h of glycolated water are treated in the glycolated water treatment column of Example 1. 7.65 kg/h of a gaseous stream at a temperature of 137° C. and a pressure of 3.2 bars are withdrawn from the top of that column. This stream practically consisting of steam is introduced into the ethylene oxide desorption column.

At the bottom of the glycolated water treatment column, an aqueous stream containing by weight 90% of ethylene glycol is collected at 180° C. and at a rate of 0.445 kg/h.

In order for such a result to be obtained, there is being furnished an amount of heat energy equivalent to the one which would permit obtaining the same effectiveness of ethylene oxide recovery without implementing the invention, but only a dilute aqueous ethylene glycol solution containing only 7.3% of ethylene glycol by weight.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A process for the separation of ethylene glycol from glycolated water containing salts obtained from the bottom of an ethylene oxide desorption column in a process for the manufacture of ethylene oxide by catalytic oxidation of ethylene by oxygen in the vapor phase comprising feeding said glycolated water; without prior separation of the salts contained therein, directly from the bottom of said ethylene oxide desorption column into the top of an ethylene glycol separation column having therebelow up to 12 theoretical plates and adding sufficient indirect heat to said glycolated water to form two streams; a first gaseous stream consisting essentially of steam which is removed from the top of said ethylene glycol separation column and introduced into said ethylene oxide desorption column to serve therein as the desorption fluid and a second aqueous stream containing from about 40% to 90% by weight of ethylene glycol and salts which is removed from the bottom of said ethylene glycol separation column; the mean absolute pressure in said ethylene glycol separation column being at least equal to the pressure of said ethylene oxide desorption column.

2. The process of claim 1 wherein the glycolated water contains sodium or potassium salts resulting from the addition of either sodium or potassium hydroxide to the glycolated water in order to prevent corrosion by carbon dioxide or the carboxylic acids which it contains.

3. The process of claim 1, wherein the mean absolute pressure in the ethylene glycol separation column is lower than 6 bars.

* * * * *